United States Patent [19]

Dutcher

[11] 4,135,518
[45] Jan. 23, 1979

[54] BODY IMPLANTABLE LEAD AND ELECTRODE

[75] Inventor: Robert G. Dutcher, Columbia Heights, Minn.

[73] Assignee: Medtronic, Inc., Minneapolis, Minn.

[21] Appl. No.: 688,807

[22] Filed: May 21, 1976

[51] Int. Cl.² ............................................. A61N 1/04
[52] U.S. Cl. .................................... 128/418; 128/404; 128/419 P
[58] Field of Search ...................... 128/404, 418, 419 P

[56] References Cited

U.S. PATENT DOCUMENTS

| 3,749,101 | 7/1973 | Williamson | 128/418 |
| 3,757,789 | 9/1973 | Shanker | 128/404 |
| 3,902,501 | 9/1975 | Citron et al. | 128/418 |
| 4,011,875 | 3/1977 | Lehr | 128/418 |

Primary Examiner—William E. Kamm
Attorney, Agent, or Firm—Lew Schwartz; Joseph F. Breimayer; Harry W. Barron

[57] ABSTRACT

A body implantable, intravascular lead affixed with a pin or pins at its proximal end adapted to be connected to a pulse generator and with an electrode or electrodes at its distal end adapted to be placed in contact with the endocardium. An electrical conductor(s) encased within a nonconductive material substantially inert to body fluids and tissues electrically connects the electrode(s) with the pin(s) and is comprised of a first length of resilient conductor having a first flexibility and an axial mechanical loading characteristic and a second length of the conductor having a second flexibility greater than the first flexibility and incapable of sustaining the axial mechanical loading characteristic. A dumbbell shaped electrode body provides sufficient size and weight to maintain the distal end of the lead in the apex of the right ventricle.

12 Claims, 6 Drawing Figures

BODY IMPLANTABLE LEAD AND ELECTRODE

BACKGROUND OF THE INVENTION

This invention relates to a lead bearing electrode(s) adapted to be connected to an electrical device and to contact a living organ to receive or conduct electrical signals there between. Notwithstanding its various uses, this invention will be described as an endocardial pacing and sensing lead for connecting a cardiac pacemaker pulse generator to cardiac tissue.

Body implantable cardiac pacemaker leads are quite well known, their construction and function being described at length in medical journals during the past 15 years. The standard endocardial lead is of the type shown is U.S. Pat. No. 3,348,548, for example, and comprises lengths of coiled wire conductors extending between a proximal pin(s) adapted to be connected to a pulse generator and a distal electrode(s) adapted to contact the endocardium of the heart. The lead is inserted and guided through a selected vein of the body until the distal end thereof is lodged in the apex of the right ventricle of the heart. A material, such as silicone rubber, that is both electrical insulating and impervious to body fluids and tissue encases the coiled wire conductor, either by a molding process or by insertion of the coiled wire conductor in a length of hollow silicone rubber tubing. In either case, a lumen extends down the center of the coiled wire conductor into which a stylet is advanced prior to insertion of the lead into the patient's vein to advance the lead through the patient's vein and to place the distal end of the lead bearing the electrode(s) at the desired position in the patient's heart.

Coiled wire conductor endocardial leads of the type disclosed in the aforementioned U.S. Pat. No. 3,348,548 possess a first flexibility and, when attached at their pins to a pulse generator, possess an axial mechanical loading force transmitted from the point of immobilization of the pulse generator down the length of the lead to its distal end. In chronic use of such leads, it has been observed that the contractions of the heart against the distal end of the lead and the axial mechanical force applied thereto may traumatize the tissue in contact with the distal end. The traumatized tissue may form a ball of scar (fibrous) tissue around the electrode(s) to reduce the stress placed upon the endocardium below the tissue damage limit. In chronic experience, it is observed that the threshold currents sufficient to stimulate the heart increase as the scar tissue is formed until the thickness of the scar tissue stabilizes. The required energy to stimulate the heart is thereby increased because of the additional potential drop across the nonresponsive scar tissue between the electrode surface and responsive cardiac cells. A discussion of this mechanism in conjunction with the realization of optimum electrode surface area appears in the paper entitled "Comparison of Power Sources for Advanced Pacemaker Applications" by Rasor, Spickler and Clabaugh (procedings of the Seventh Intersociety Energy Conversion Engineering Conference, January, 1972, pages 752-760).

However, it remains the consensus that the coiled wire conductor is necessary to restrain the stiffening stylet from perforating the silicone rubber encasing material at any point along the length of the lead where it departs radically from a straight line. In the implantation procedure, once the physician has advanced the distal end of the lead into the right ventricle, he may find it necessary to withdraw the stylet, form a curve at the distal end thereof, and reinsert the stylet into the lumen of the lead down to the distal end thereof. If the side wall of the lead is not sufficiently strong, the stylet, especially with the curvature in the distal end thereof, may well pass through the side wall of the lead and snag in the vein. The article "Technique for Insertion of Transvenous Endocardial Pacemakers" by N. P. D. Smyth, M.D. (*Journal of Thoracic and Cardiovascular Surgery*, vol. 51, pp 755-758, 1966) depicts the tortuous transvenous path of endocardial leads.

It has been recognized that the flexibility of the coiled wire conductor may be increased by reducing its diameter. However, reduction in the diameter increases the wire's electrical resistance and the resulting waste of energy is unacceptable.

It has also been know that there are other advantageous and flexible lead conductor configurations. For example, U.S. Pat. No. 3,572,344 discloses a lead construction commonly used in myocardial leads, where stylets are unnecessary, commonly referred to as the "tinsel wire" lead. The tinsel wire lead conductor has a nonconductive fiber core around which are wrapped a plurality of conductor strands. Each strand comprises an electrical conductor strip itself wrapped around a separate nonconductive fiber core. The strands and strips are helically wound about the main core and the windings are spaced one from the other. Leads constructed of such tinsel wire are notably free from axial mechanical loading forces and are resistant to fracture. Such leads may retain their strength and durability and still be manufactured in a diameter somewhat smaller than that typically used in coiled wire construction leads. Unfortunately, the tinsel wire construction is incapable of restraining a stylet from passing through the side wall of the lead. No advantage is known to obtain over coiled wire conductor leads by making the tinsel wire lead strong enough to withstand such puncture, either by increasing the number of tinsel wire conductor strand, their thickness or other properties or by adding a puncture-resistant nonconductive tube for the lumen to the construction of the lead.

The body implantable lead of the present invention combines all the advantages of both types of lead construction with none of the attendant disadvantages set forth above. One of the features of the present invention is the provision of a puncture-resistant lumen through that portion of the lead that may be susceptible to puncture and the elimination of the axial mechanical load of the lead on the endocardium. Another feature of the invention is that the conductors used in the lead comprise reliable designs that enjoy demonstrated reliability in chronic use permitting easy placement of the lead in the heart according to well-known techniques.

SUMMARY OF THE INVENTION

The above features and advantages of the present invention, as well as the others, are accomplished by providing a body implantable, intravascular lead of the type having at least one electrically conductive pin at its proximal end adapted to be connected to a source of electrical energy and/or sensing circuit, and at least one electrode affixed to the distal end thereof, adapted to be firmly lodged in contact with endothelial tissue, with an improvement in the construction of the lead comprising means for eliminating axial mechanical loading of the lead on the endothelial tissue in contact with the distal end thereof.

Preferably, the improved lead comprises first and second lengths of electrical conductor respectively possessing the properties of receiving means for stiffening the lead during its introduction and means for eliminating the mechanical load placed on the endothelial tissue in contact with the distal end thereof. More particularily, the first length of electrical conductor comprises coiled wire conductor(s) having a first flexibility extending a first predetermined length along the body of the lead, and the second length comprises the second wire conductor(s) possessing a second flexibility greater than the first flexibility sufficient to relieve the axial mechanical load imposed on the distal end of the lead by the first length of coiled wire conductor.

A further feature of the present invention comprises an electrode body generally cylindrical in shape having a large tissue contacting surface area, thereby reducing tissue contact pressure, but a smaller, conductive electrode surface area, the cylindrical body further comprising flange means for receiving tissue bearing against the body. The flange means comprises a waist portion of relatively narrow diameter near the middle of the body, the body's diameter gradually increasing from the waist portion to the tip and to the proximal end of the body, thereby creating rearward and foreward extending conical flanges. Body tissue bearing against the waist portion and along the conical surfaces of the flanges maintain the electrode body in position thereby reducing incidences of dislodgement.

Other features, advantages and objects of the present invention will hereinafter become more fully apparent from the following description of the drawings, which illustrate preferred embodiments thereof.

DESCRIPTION OF THE PREFERRED EMBODIMENTS

Figure 1:
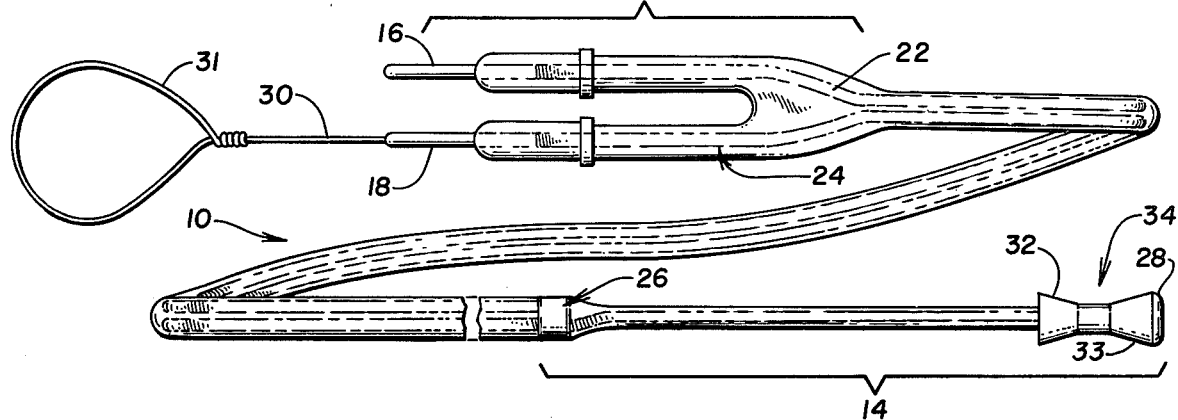
FIG. 1 shows a preferred embodiment of a bipolar version of the body implantable, intravascular lead of the present invention including a stylet advanced in one lumen thereof.

Referring now to the first preferred embodiments of the invention depicted in FIG. 1, there is shown a bipolar, intravascular endocardial lead 10 and stylet 30 comprising a proximal end portion 12, a distal end portion 14, and the electrical conductors extending there between. The proximal end portion 12 comprises a pair of hollow pins 16 and 18 adapted to be connected to the terminals of a bipolar pacemaker pulse generator, such as the Model 5944 bipolar, demand, pulse generator manufactured by Medtronic, Inc. The pins 16 and 18 are electrically connected to a pair of electrical conductors 22 and 24. The electrical conductor 22 extends to and is electrically connected with a ring electrode 26, whereas the electrical conductor 24 extends to and is electrically connected with the distal electrode 28. The ring electrode 26 and distal electrode 28 are composed of electrically conductive materials such as platinum or a platinum alloy or a low temperature isotopic conductive carbon and are adapted to pass electrical pacing stimuli developed by the pulse generator to the heart and/or to transmit naturally occurring electrical signals from the heart to the pulse generator. Throughout the length of the lead 10, the conductors are encased in a suitable, body compatible electrically insulating material such as silicone rubber or a polyurethane compound, that is substantially inert to body fluids and tissues.

The stylet 30 is depicted as extended into the hollow pin 18 and through the cavity or lumen of a coiled wire conductor 24. As mentioned hereinbefore the stylet 30 comprises a length of steel wire that, when inserted in the lead 10, imparts stiffness thereto. A loop 31 is formed at the proximal end of the stylet 30 to enable the physician to rotate the stylet 30 during the placement procedure to orient the tip of the lead, under fluroscopy, to a desired location in the heart, in the well-known implantation procedure.

In accordance with the teachings of the present invention, the distal end portion 14 of the lead 10 is more flexible than the remaining length of the lead 10 and incapable of sustaining any substantial axial mechanical force along its length. This section of the lead 10 extending between the ring electrode 26 and the distal or tip electrode 28 may be comprised of a hollow tinsel wire conductor adapted to receive the corresponding terminal end portion of the stylet 30. The distance between the ring electrode 26 and the tip electrode 28 may vary, but is expected to be no more than ten centimeters.

However, the remaining length of conductor 24 extending between the ring electrode 26 and the pin 18 possesses strength and other characteristics allowing the insertion of the stylet 30 through the lead without perforating the lead wall. Such electrical conductor 24 may comprise either the conventional coiled wire conductor, electrically and mechanically connected to the hollow tinsel wire conductor at or near the ring electrode 26, or that portion of the lead 10 may comprise an extension of the hollow tinsel wire conductor in which a puncture-resistant lumen is formed.

The other electrical conductor 22 may be formed of a length of coiled wire conductor or reinforced, hollow tinsel wire conductor electrically connected between the pin 16 and the ring electrode 26.

Alternatively, the conductor 24 extending through the distal end portion 14 may take the form of coiled wire possessing higher flexibility than the length of coiled wire conductor 24 extending between pin 18 and electrode 26. This may be accomplished by making the diameter of the wire itself (not the diameter of the coil) extending through the distal end portion 14 smaller than the remaining length of wire. The electrical resistance of the smaller diameter wire will, however, be greater than that of the normal diameter wire, and accordingly energy transfer efficiency may be sacrificed. However, since the total resistance is dependent on length of the wire, energy losses may be minimized by appropriate selection of the length of distal end portion 14. This alternative design may lend itself to manufacturing efficiencies if the entire length of coiled wire conductor could be made of the same length of wire having the respective lengths of differing diameters.

A second alternative design contemplates an enlarged diameter coil of the conductor 24 extending through the distal end portion 14. The larger diameter coil may possess higher flexibility than the remaining length of conductor 24 of smaller coil diameter.

The distal electrode 28 may take any form, shape or size that is considered to be desirable under the circumstances. In FIG. 1, the distal electrode body 34 is dumbbell shaped having rearwardly and forwardly extending flanges 32 and 33 adapted to lodge in the trabeculae of the right ventricle. The conductive electrode 28 is in the form of a ring on the circumference of the tip of the dumbbell shaped body 34. The body 34 may be of a material not itself susceptible to the growth and encapsulation by fibrotic tissue, and may be of such a weight and size as to enhance the chances that it will not be dislodged from the apex of the right ventricle.

The dumbbell shaped body 34 possesses further advantages, in that the forwardly extending flange 33 allows the use of a relatively large and blunt tip that reduces the pressure applied to the myocardium thereby reducing the chances of perforation of the myocardium. The narrow waist 35 of the body 34 accommodates the ingrowth or inward pressure of body tissue, e.g. trabeculae of the right ventricle, and the body 34 is less likely to be dislodged by the beating action of the heart.

Figure 2:
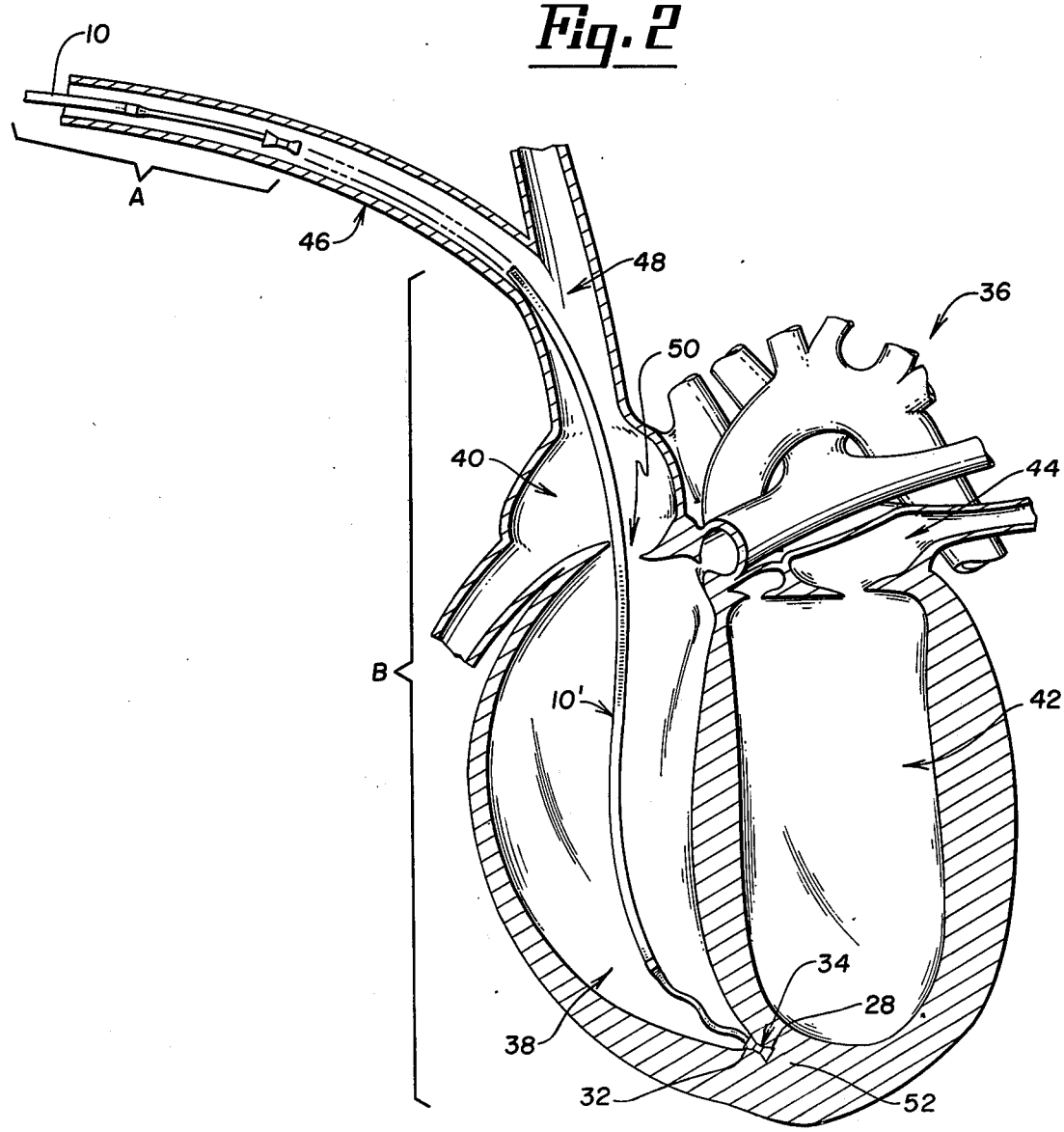
FIG. 2 shows the lead of FIG. 1 being advanced through a vein and lodged in the right ventricle of the patient's heart, respectively.

The objects and advantages of the novel lead of the present invention are more clearly understood in reference to FIG. 2. In FIG. 2, the lead 10 is shown in a first position A during its introduction through the venous system of the patient and in a second position B depicting lodgment of the distal end in the apex of the right ventricle.

In FIG. 2, the heart 36 in cross section comprises the four chambers, namely, the right ventricle 38, the right atrium 40, the left ventricle 42 and the left atrium 44. In the placement of an endocardial lead, it is preferable to use a venous approach on the low pressure side of the heart, that is, through a vein such as the right or left external jugular vein or the right or left cephalic vein 46, the superior vena cava 48, the right atrium 40, the tricuspid valve 50, to the right ventricle 38. During introduction of the lead 10, it must travel a convoluted course through the veins and must pass through the valve 50 without causing any damage to the tissue. It is also desirable that the lead 10 have a small cross section so that it will easily pass without causing excessive stretching of the veins.

In position A of FIG. 2, the distal end portion 14 of the lead 10 is shown in part. As it is advanced, the stylet 20 maintains the rigidity of the lead 10 and particularly the flexible distal portion 14, thereof, so that the portion 14 does not buckle in the vein, and passes readily through the tricuspid valve 50. As the lead 10 is advanced through the venous system, it may travel through a convoluted path having several twists and turns.

In position B of FIG. 2, the lead 10 is depicted in its fully advanced position wherein the tip electrode 28 is lodged in contact with the apex 52 of the right ventricle. It will be understood that the depiction of the heart 36 is figurative and that trabecular tissue at or near the apex 52 will intimately contact the sides and flange 32 of the body 34 at the distal end of the lead 10.

As shown in position B of FIG. 2, the distal end portion of the lead 10 is flexed following withdrawal of the stylet 30 and a slight advancement and securement of the lead 10 thereafter. The flex or curvature in the distal end portion of the lead 10 will change due to the flexibility of that portion of the lead, as the heart contracts and expands. The flexibility of the distal segment of the lead 10 does not result in significant axial mechanical force of the distal end of the lead on endocardial tissue. Therefore, assuming that the distal electrode is securely placed in the apex 52, the lead 10 should not traumatize the immediate endocardium in contact therewith, and chronic pacing thresholds should remain closer to the low thresholds initially encountered in the use of conventional endocardial leads. If it is necessary to withdraw the stylet 20 from the lead 10 to curve it, or for any other reason, and to reinsert the stylet 20, the design of the lead of the present invention allows the reintroduction of the stylet without fear of puncturing the lead through most of its length. Since the distal segment of the lead 10 may be straightened by slight withdrawal of the lead under fluoroscopy it is unlikely that a puncture will occur in the distal segment 14, and it will be possible to reposition the distal end relatively simply.

Figure 3:
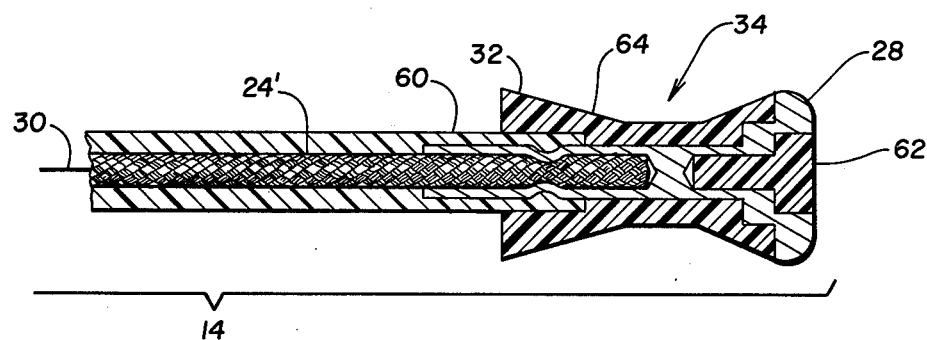
FIG. 3 shows in part, an inside elevation, partly in longitudinal section, of the distal end portion of the lead of FIG. 1.

Referring now to FIG. 3, it is shown in detail the construction of body 34 and its attachment to the conductor 24'. As mentioned hereinbefore, the conductor 24' may be of tinsel wire with a hollow lumen down its center for accommodating the distal portion of the stylet 20. A thin layer 60 of silicone rubber or polyurethane compounds encapsulates the distal segment 14, of the conductor 24'. Likewise, the body 34 may be composed of silicone rubber or a polyurethane compound that is nonconductive and biocompatible. The ring electrode 28 is shown in cross-section in FIG. 3. The central portion 62 within the ring 28 is likewise filled with a nonconductive body compatible material. The ring electrode 28 is thus exposed only along the periphery of the body 34 and is adapted by its shape to at least contact body tissue at some one or more points along its circumference. The ring electrode 28 is electrically and mechanically connected to the end of conductor 24'. The conductor 24' is inserted into the hollow bore of the extension 64 of the ring electrode 28, and the extension 64 is crimped about the circumference of the conductor 24'.

Figure 4:
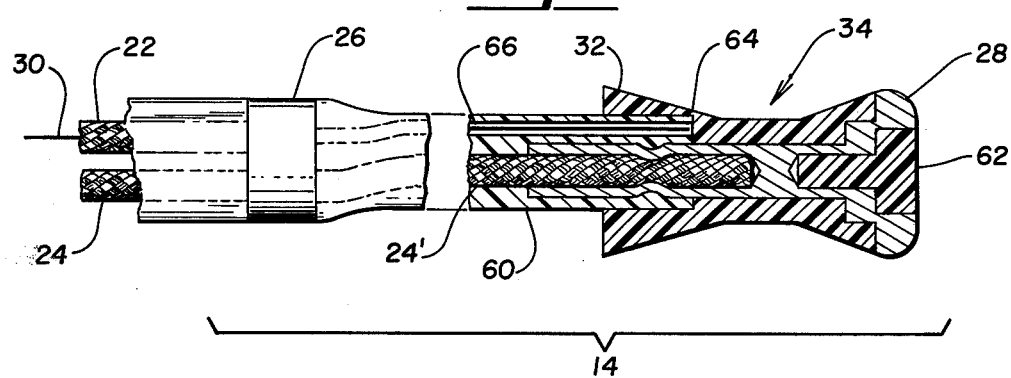
FIG. 4 shows in part, a further inside elevation, partly in longitudinal section of a further embodiment of the distal end portion of the lead of the present invention.

Referring now to FIG. 4, there is shown an alternative version of the distal electrode body 34 and the lumen for the stiffening stylet. As in the embodiment of FIGS. 1 and 3, the conductor 22 extends to, and is in electrical contact with the ring electrode 26, whereas the conductor 24' extends into the bore of the extension 64 of the ring electrode 28. However, the embodiment of FIG. 4 contemplates the use of a conventional conductor, such as tinsel wire throughout its length from the pin 18 to the ring electrode 28. In this embodiment, there would be no lumen in the pin 18 or the tinsel wire conductor 24. However, the lumen in the coil wire conductor 22 would extend in a further lumen 66 in the material 60 from the ring electrode 26 into the flange 32 of the terminal body 34. Thus, during introduction and/or placement of the lead, the stiffening stylet 30 would be advanced through the coil wire conductor 22 to the ring electrode 26 and from the ring electrode 26 to the flange 32 through the lumen 66, thereby imparting stiffness to the distal segment of the lead.

Figure 5:
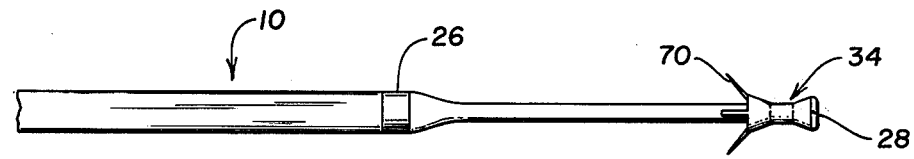
FIG. 5 shows in part, a variation on the lead of FIG. 1, including tine elements for engaging endothelial tissue to retain the distal electrode of the lead in contact with endothelial tissue.

Referring now to FIG. 5, there is shown a modification of the flange 32 of the body form 34 designed to affix the distal electrode 28 in intimate contact with the endocardium. A number of tines 70 extend radially from the flange 32 of the body 34. The tines 70 may take the form of those depicted in U.S. Pat. No. 3,902,501, although it will be understood that other forms of stabilizing the electrode, such as those depicted in the aforementioned by Rasor, et al, article could as well be employed.

Figure 6:
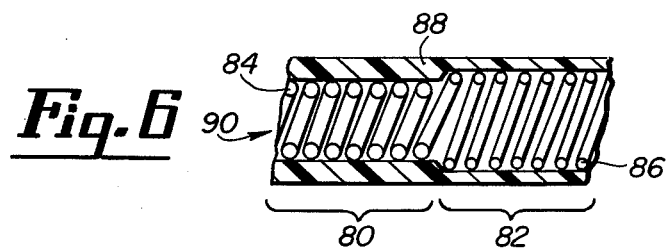
FIG. 6, shows in part an inside elevation in section of a further embodiment of the lead conductor construction.

Referring now to FIG. 6, there is shown a further construction of a lead conductor of the present invention having a first conductor segment 80 (like conductor 24 of FIG. 1) having a first flexibility and a second conductor segment 82 having a second flexibility greater than the first flexibility. The segment 80 comprises a coiled wire conductor 84 the wire of which has a first cross-sectional area and diameter; likewise the segment 82 comprises a coiled wire conductor 86 having a second cross-sectional area and diameter that is smaller than the first diameter. In other words, wire 86 is thinner than wire 84. The first segment 80 is of ordinary lead wire construction and dimensions as used in the Medtronic ® Model 6901 and 6907 endocardial pacing leads widely available prior to the filing date of this application which, while regarded as flexible as possible at the time, can bear an axial mechanical force against the endocardium, creating the problems mentioned previously. The second segment 82 may be drawn from the same continuous wire stock as the first segment 80, but the smaller diameter of its coil wire 86 makes it more flexible than the coiled wire 84. Therefore, the segment 82 does not exert an axial mechanical force or transmit that presented by the first segment 80 against the endocardium. The coiled wires of both segments are covered by insulating sheath 88 in the well known manner and present a lumen 90 for the conventional introduction of a stylet (not shown).

FIG. 6 also illustrates a second approach to increasing the flexibility of the second segment 82, namely a larger outside diameter of the coil created by winding the wire 86 through the corresponding outside diameter of the coil of wire 84. The increase in the outside coil diameter and the decrease in wire diameter in segment 82 is illustrated in the same FIG. 6 merely for convenience and it will be understood that either or both approaches may be taken in practice.

It will be understood that the teachings of the present invention may be applied to unipolar lead designs as well as variations on the bipolar endocardial lead designs depicted for purposes of illustration in the drawings. Furthermore, it will be well understood that alternative conductor forms may be employed in the practice of the invention. For example, a coaxial lead design may be provided wherein a distal flexible segment of lead incapable of applying an axial mechanical load on the distal electrode may form one or the other of the coaxial conductors through or along which the stylet may be advanced.

It should be further understood, of course, that the foregoing disclosure relates only to the best modes and only to the inventor of many possible modes of practicing the invention, and that numerous modifications may be made therein without departing from spirit and scope of the invention as set forth in the appended claims.

What is claimed is:

1. In a body implantable lead of the type including a proximal end adapted for connection to an electrical device and a distal end adapted to contact living tissue and a conductor extending between the proximal and distal ends, the improvement comprising a first segment of said conductor having a first flexibility and an axial mechanical loading characteristic and a second segment of said conductor having a second flexibility greater than said first flexibility and incapable of sustaining said axial mechanical loading characteristic.

2. A body implantable lead comprising:
    (a) a length of electrical conductor having a proximal end and a distal end, said electrical conductor comprising a first segment of conductor having a first flexibility and capable of bearing an axial mechanical force and a second segment of conductor having a second flexibility greater than said first flexibility and incapable of sustaining said axial mechanical force;
    (b) connector means for electrically connecting said proximal end of said electrical conductor to an electrical device for conducting electrical signals to and from said electrical device;
    (c) electrode means electrically connected to the distal end of said conductor for transmitting and receiving electrical signals to and from body tissue; and
    (d) means substantially inert to body fluids and tissues for electrically insulating said electrical conductor from body tissue.

3. The body implantable lead of claim 2 wherein said first segment of electrical conductor comprises a wire having a first cross-sectional area and said second segment of said conductor comprises wire having a second cross-sectional area smaller than said first cross-sectional area of the wire of said first segment.

4. The body implantable lead of claim 3 wherein said conductor further comprises a coiled wire with a lumen extending down the center of said first and second coiled wire segments and stylet wire means for selective insertion into said lumen for selectively imparting stiffness to said body implantable lead.

5. The body implantable lead of claim 2 wherein said first segment of electrical conductor comprises a wire having a first outside coil diameter and said second segment of said conductor comprises wire having a second outside coil diameter larger than said first outside coil diameter of the wire of said first segment.

6. The body implantable lead of claim 5 wherein said conductor further comprises a coiled wire with a lumen extending down the center of said first and second coiled wire segments and stylet wire means for selective insertion into said lumen for selectively imparting stiffness to said body implantable lead.

7. The body implantable lead of claim 2 wherein said distal end of said lead further comprises:
    (a) a generally elongated, cylindrical body of electrically insulating material extending a predetermined distance along said distal end of said conductor and having a predetermined diameter at a point between the two ends thereof;
    (b) conductive electrode means on the surface of said elongated body having a surface area smaller than the surface area of said body; and
    (c) means extending along said length of said body for engaging body tissue and preventing the dislodgement of said body from said tissue.

8. A body implantable lead of material substantially inert to body fluids and tissue having a length of electrically insulated, flexible conductor, a connector pin at the proximal end of said conductor, an electrode adapted to contact the tissue of a living body at the distal end of said conductor, a lumen extending the length of the insulated conductor adapted to receive a stiffening stylet for straightening and imparting stiffness to said lead, said flexible conductor further comprising:

(a) a first segment of coiled wire extending through a predetermined length of said lead, said coiled wire having a first flexibility imparting an axial mechanical loading force to said lead; and (b) a second segment of conductor electrically connected to said first segment, said second segment having a second flexibility exceeding the first flexibility of said first segment rendering said second segment incapable of sustaining said axial mechanical loading force.

9. The body implantable lead of claim 8 wherein said lumen extends through said coiled wire of said first segment of said conductor and along said second segment of said conductor to said distal end of said lead.

10. The body implantable lead of claim 9 wherein said second segment comprises a tinsel wire and said lumen extends through said coiled wire and axially with respect to said tinsel wire.

11. In a body implantable lead of the type including a proximal end adapted for connection to an electrical device, a distal end adapted to contact living tissue and a conductor extending between the proximal and distal ends thereof, the improvement in said distal end comprising:

(a) a generally elongated, cylindrical body of electrically insulating material extending a predetermined distance along said distal end of said conductor and having a predetermined diameter at a point between the two ends thereof; and having (b) conductive electrode means on the surface of said elongated body having a surface area smaller than the surface area of said body;

(d) a first generally conically shaped flange extending from one end of said body towards said point of predetermined diameter; and (e) a second generally conically shaped flange extending from the other end of said body towards said point of predetermined diameter.

12. A body implantable lead of claim 11 wherein the diameter at the distal end of said body exceeds the diameter at said point.

* * * * *